US012582817B2

(12) United States Patent
Pasquali et al.

(10) Patent No.: US 12,582,817 B2
(45) Date of Patent: Mar. 24, 2026

(54) USE OF ELECTRICALLY CONDUCTIVE MATERIALS FOR ELECTROPHYSIOLOGY

(71) Applicants:William Marsh Rice University, Houston, TX (US); Baylor College of Medicine, Houston, TX (US); Texas Heart Institute, Houston, TX (US)

(72) Inventors: Matteo Pasquali, Houston, TX (US); Mehdi Razavi, Houston, TX (US); Flavia Vitale, Houston, TX (US); Colin Christopher Young, Houston, TX (US); Mark David Mccauley, Houston, TX (US)

(73) Assignees: William Marsh Rice University, Houston, TX (US); Baylor College of Medicine, Houston, TX (US); Texas Heart Institute, Houston, TX (US)

( * ) Notice: Subject to any disclaimer, the term of this patent is extended or adjusted under 35 U.S.C. 154(b) by 907 days.

(21) Appl. No.: 17/811,780

(22) Filed: Jul. 11, 2022

(65) Prior Publication Data

US 2022/0339436 A1 Oct. 27, 2022

Related U.S. Application Data

(63) Continuation of application No. 15/022,010, filed as application No. PCT/US2014/055893 on Sep. 16, 2014, now abandoned.

(60) Provisional application No. 61/942,223, filed on Feb. 20, 2014, provisional application No. 61/878,259, filed on Sep. 16, 2013.

(51) Int. Cl.
| | |
|---|---|
| *A61N 1/00* | (2006.01) |
| *A61B 17/06* | (2006.01) |
| *A61N 1/05* | (2006.01) |

(52) U.S. Cl.
CPC ...... *A61N 1/0587* (2013.01); *A61B 17/06166* (2013.01); *A61N 1/05* (2013.01); *A61N 1/0551* (2013.01); *A61N 1/056* (2013.01)

(58) Field of Classification Search
CPC ...... A61N 1/0587; A61N 1/05; A61N 1/0551; A61N 1/056; A61B 17/06166
See application file for complete search history.

(56) References Cited

U.S. PATENT DOCUMENTS

| | | | | |
|---|---|---|---|---|
| 2003/0170166 A1* | 9/2003 | Smalley | .................. | D01F 11/12 |
| | | | | 423/447.2 |
| 2013/0183352 A1* | 7/2013 | Xie | ....................... | A61L 27/306 |
| | | | | 623/23.72 |

* cited by examiner

*Primary Examiner* — Scott M. Getzow
(74) *Attorney, Agent, or Firm* — Osha Bergman Watanabe & Burton LLP

(57) ABSTRACT

A method of improving electrical conduction across an impaired region of a tissue (e.g., myocardial tissue), includes applying an electrically conductive wiring (e.g., carbon nanotube fibers) across the impaired region. The electrically conductive wiring can become associated with non-impaired regions of the tissue on opposite sides of the impaired region by suturing. The method can also be utilized to treat or prevent cardiac arrhythmia in a subject (e.g., ventricular arrhythmia). The electrically conductive wiring includes carbon nanotubes, such as carbon nanotube fibers. Such electrically conductive wiring can be used to transmit electrical signals to a tissue or sense electrical signals from the tissue. Suture threads including carbon nanotubes, such as carbon nanotube fibers, are provided.

20 Claims, 13 Drawing Sheets

30

40

36

38

32

34

40

B

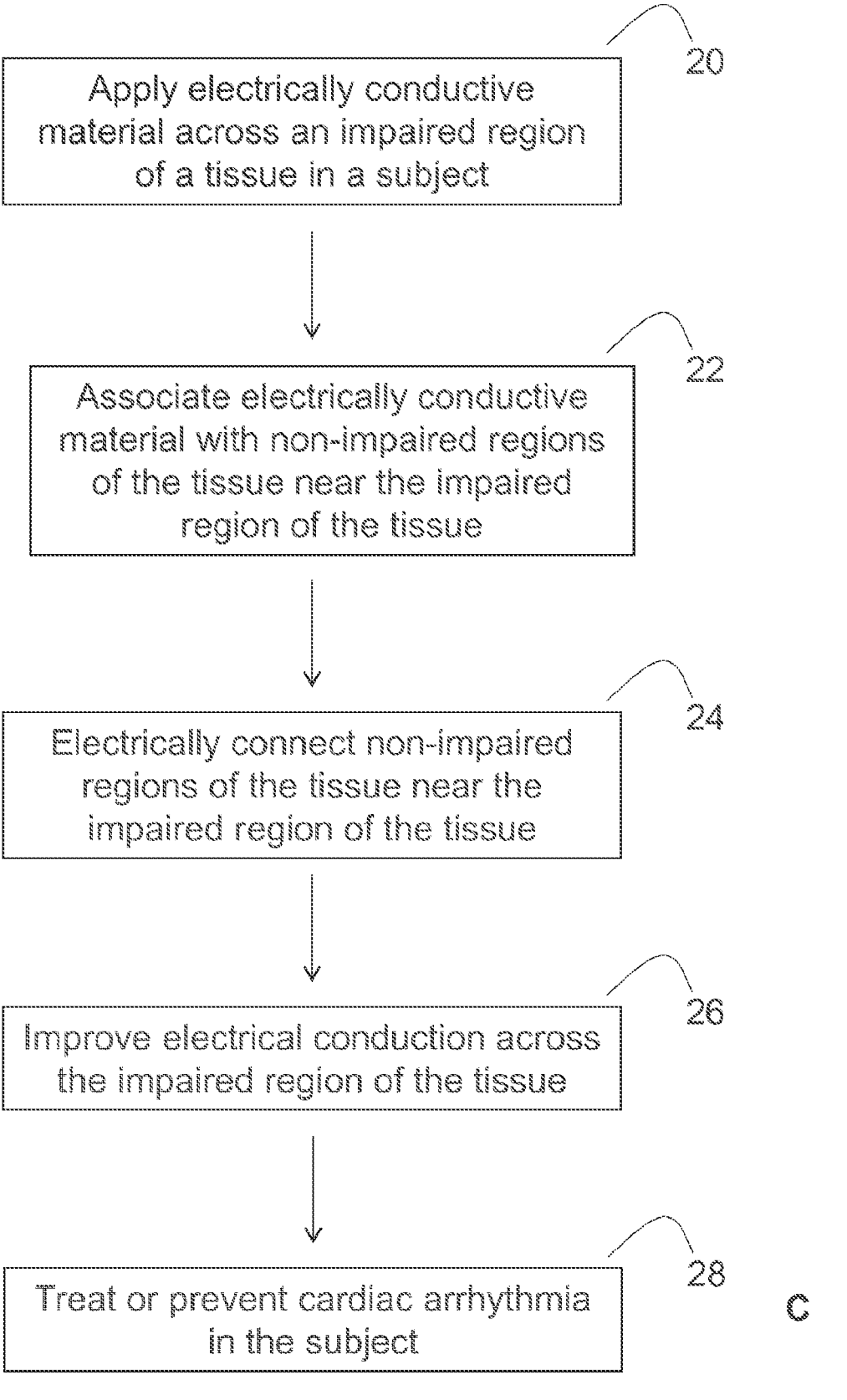

20

Apply electrically conductive
material across an impaired region
of a tissue in a subject

22

Associate electrically conductive
material with non-impaired regions
of the tissue near the impaired
region of the tissue

24

Electrically connect non-impaired
regions of the tissue near the
impaired region of the tissue

26

Improve electrical conduction across
the impaired region of the tissue

28

Treat or prevent cardiac arrhythmia
in the subject

RF lesion    CNTf pacing

CNTf conduction

A 10 mm

B

C

D

A

B

Baseline

A

RF lesion

B

CNT fiber

C

A

B

Pacing with
CNT fibers

A

B

USE OF ELECTRICALLY CONDUCTIVE MATERIALS FOR ELECTROPHYSIOLOGY

CROSS-REFERENCE TO RELATED APPLICATIONS

This application claims priority to U.S. Provisional Patent Application No. 61/878,259, filed on Sep. 16, 2013; and U.S. Provisional Patent Application No. 61/942,223, filed on Feb. 20, 2014. The entirety of each of the aforementioned applications is incorporated herein by reference.

BACKGROUND

Current methods of treating cardiac arrhythmia suffer from numerous limitations. Current methods of sensing electrical signals from cardiac tissues and transmitting electrical signals to cardiac tissues also suffer from numerous limitations. Various embodiments of the present disclosure address the aforementioned limitations.

SUMMARY

In some embodiments, the present disclosure pertains to methods of improving electrical conduction across an impaired region of a tissue by applying an electrically conductive material across the impaired region. In some embodiments, the tissue includes myocardial tissue. In some embodiments, the impaired region of the tissue includes, without limitation, a scarred area, an ablated area, a bruised area, a cut area, a lesion, and combinations thereof.

In some embodiments, electrically conductive materials become associated with non-impaired regions of the tissue that are near the impaired region of the tissue. In some embodiments, electrically conductive materials become associated with non-impaired regions of the tissue that are on opposite sides of the impaired region of the tissue. In some embodiments, the association occurs by suturing.

In some embodiments, the electrically conductive materials include, without limitation, fibers, wires, metal wires, foils, metal foils, conductive polymers, carbon nanotubes, materials made from carbon nanotubes, and combinations thereof. In some embodiments, the electrically conductive materials include materials made from carbon nanotubes, such as carbon nanotube fibers.

In some embodiments, the electrically conductive materials of the present disclosure improve the electrical conduction across an impaired region of a tissue by electrically connecting non-impaired regions of the tissue near the impaired region of the tissue. In some embodiments, the electrically conductive materials improve the electrical conduction across an impaired region of a tissue by restoring or enhancing electrical conduction across the impaired region of the tissue.

In some embodiments, the present disclosure pertains to methods of treating or preventing cardiac arrhythmia in a subject by applying the electrically conductive materials of the present disclosure across an impaired region of a tissue (e.g., myocardial tissue) in the subject. In some embodiments, the subject is at risk of suffering from cardiac arrhythmia. In some embodiments, the subject is suffering from cardiac arrhythmia. In some embodiments, the cardiac arrhythmia to be treated is ventricular arrhythmia.

In some embodiments, the present disclosure pertains to electrical wirings for sensing or transmitting electrical signals. In some embodiments, the electrical wiring includes carbon nanotubes. In some embodiments, the carbon nanotubes are in the form of carbon nanotube fibers. In some embodiments, the electrical wiring includes a conductive element and one or more points of attachment. In some embodiments, the electrical wirings of the present disclosure are associated with an electrical device, such as medical devices, pacemakers, defibrillators, electrocardiographs, and combinations thereof.

In some embodiments, the present disclosure pertains to methods of transmitting electrical signals to a tissue by associating the tissue with an electrical wiring of the present disclosure, and transmitting electrical signals to the tissue through the electrical wiring. In some embodiments, the transmittal of electrical signals to the tissue includes delivery of an electrical signal from an electrical device associated with the electrical wiring (e.g., medical devices, pacemakers, defibrillators, and combinations thereof). In some embodiments where the tissue includes myocardial tissue in a subject, the methods of the present disclosure can be used for cardiac resynchronization or defibrillation in the subject.

In some embodiments, the present disclosure pertains to methods of sensing electrical signals from a tissue by associating the tissue with an electrical wiring of the present disclosure, and sensing electrical signals from the tissue through the electrical wiring. In some embodiments, the sensing of electrical signals from the tissue includes sensing the electrical signals in an electrical device associated with the electrical wiring (e.g., medical devices, pacemakers, defibrillators, electrocardiographs, and combinations thereof). In some embodiments where the tissue includes myocardial tissue in a subject, the sensing of electrical signals from the myocardial tissue includes sensing of cardiac electrical activity.

In some embodiments, the present disclosure pertains to suture threads that include carbon nanotubes. In some embodiments, the carbon nanotubes in the suture threads include carbon nanotube fibers. In some embodiments, the suture threads consist essentially of carbon nanotube fibers. In some embodiments, the suture threads only consist of carbon nanotube fibers.

DESCRIPTION OF THE FIGURES

FIG. 2A is a photograph of the left ventricle (LV) of a heart with a radiofrequency (RF) scar caused by RE ablation. A (CNT fiber has been placed across the RE scar. FIG. 2B is a photograph of the CNT fiber. FIG. 2C is a diagram showing the locations of decapolar catheters and the CNT fiber pacing leads on the ventricle of a heart prior to RE ablation. FIG. 2D is a diagram showing the locations of decapolar catheters and the CNT fiber pacing leads on the ventricle of a heart after RE ablation.

FIG. 4A is a map of the locations in the experimental area where the conduction velocity was measured. FIGS. 4B-E show the average conduction intervals measured by the 4 arrays of decapolar catheters in three animal experiments. Concentric circles represent time (in ms), whereas radial positions represent the location of the channel where intervals were measured. Brown areas in FIGS. 4C-E represent the RF lesion. Yellow circles in FIGS. 4D-E represent the locations where CNT fibers and silk sutures were implanted, respectively.

FIG. 5C shows that myocardial conduction improved only in the area where CNT fibers were sutured across the RE lesion (yellow dots pointed by yellow arrows). Activation time and propagation maps are rotated by ~90 degrees compared to the orientation shown in FIG. 2A for ease of visualization, FIG. 6A shows the experimental setup. FIG. 6B shows conduction time measured at the channels nearest to the CNT fibers. The results indicate that CNT fibers can transduce myocardial action potentials across an area of slow conduction without needing external pacing. Bars show mean±S.E.M.

FIG. 7A shows data validating myocardial pacing at 150 BPM (i.e. CL 400 ms) with CNT fibers, FIG. 7B shows data validating the sensing of myocardial potential at sinus rhythm with CNT fibers and the most proximal standard epicardial electrode.

DETAILED DESCRIPTION

Figure 1:
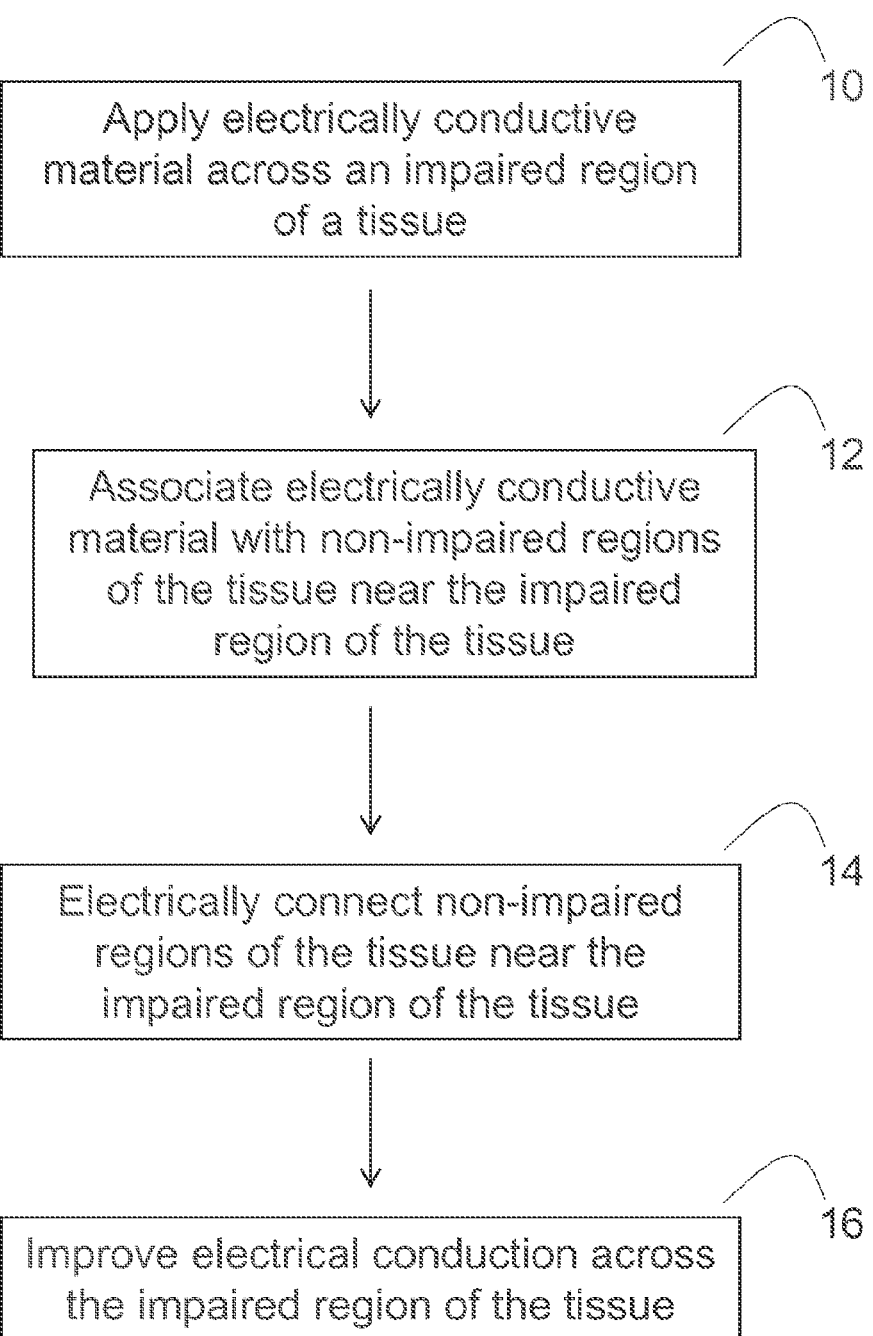
FIG. 1 provides schemes of methods of improving electrical conduction across an impaired region of a tissue (FIG. 1A), methods of treating or preventing cardiac arrhythmia in a subject (FIG. 1C), methods of sensing electrical signals from a tissue by associating the tissue with an electrical wiring that includes carbon nanotubes (FIG. 1E), and methods of sensing electrical signals from a tissue by associating the tissue with the electrical wiring (FIG. 1F). A depiction of a system for improving electrical conduction across an impaired region of a tissue is also shown (FIG. 1B). A system for sensing or transmitting electrical signals is also shown (FIG. 1D).
Figure 1:
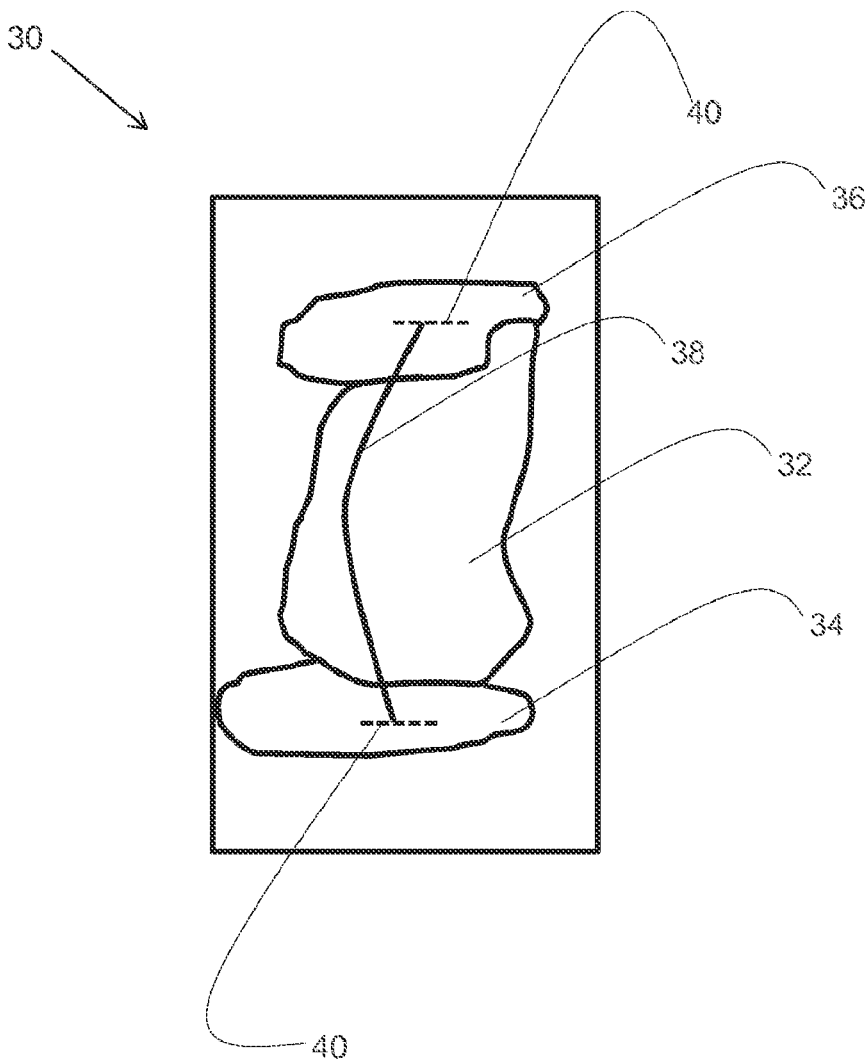
Figure 1:
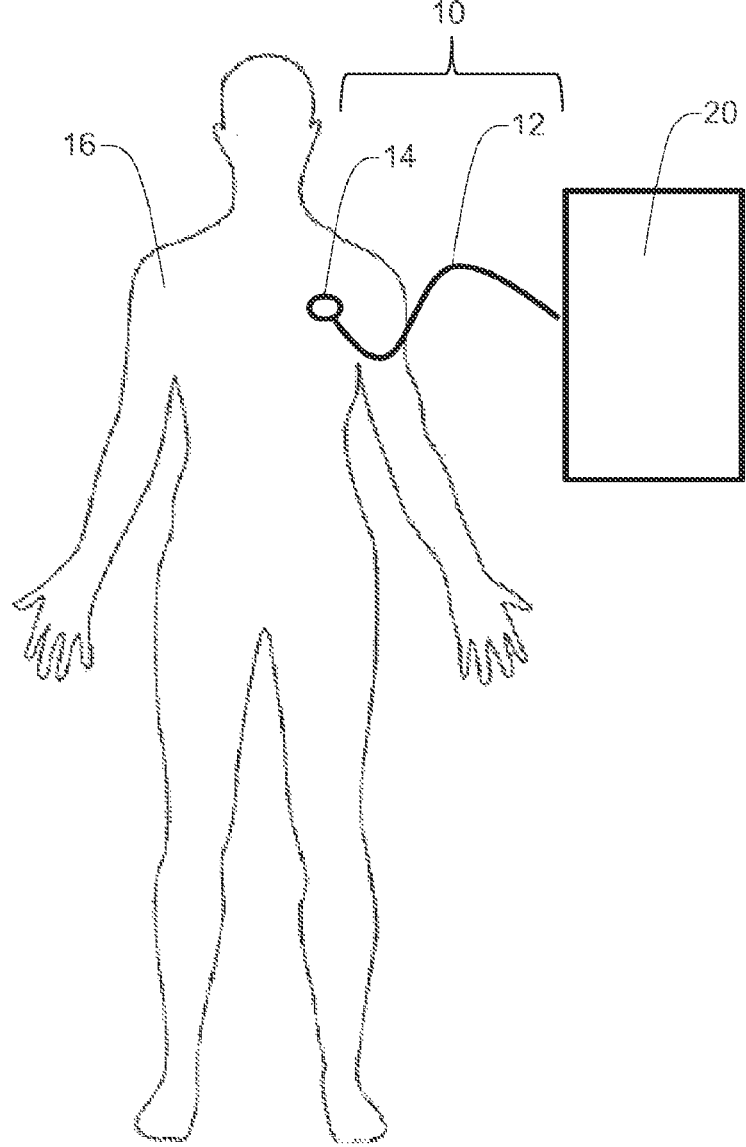
Figure 1:
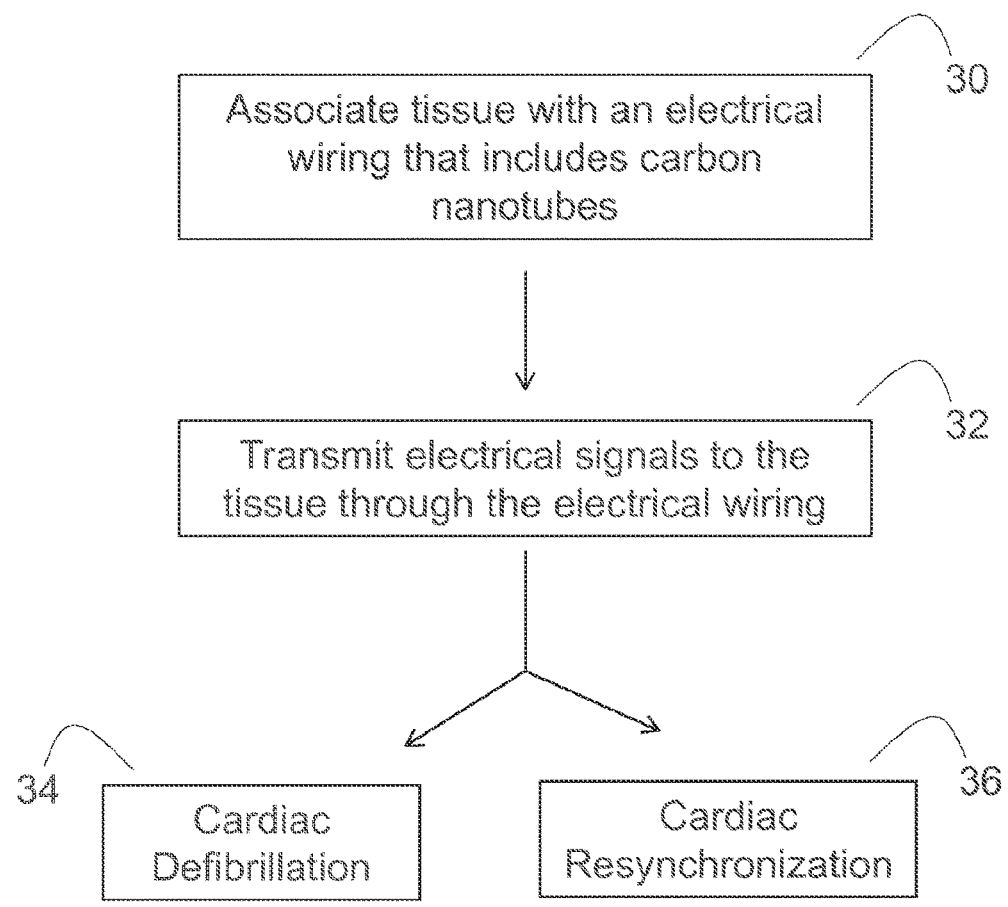
Figure 1:
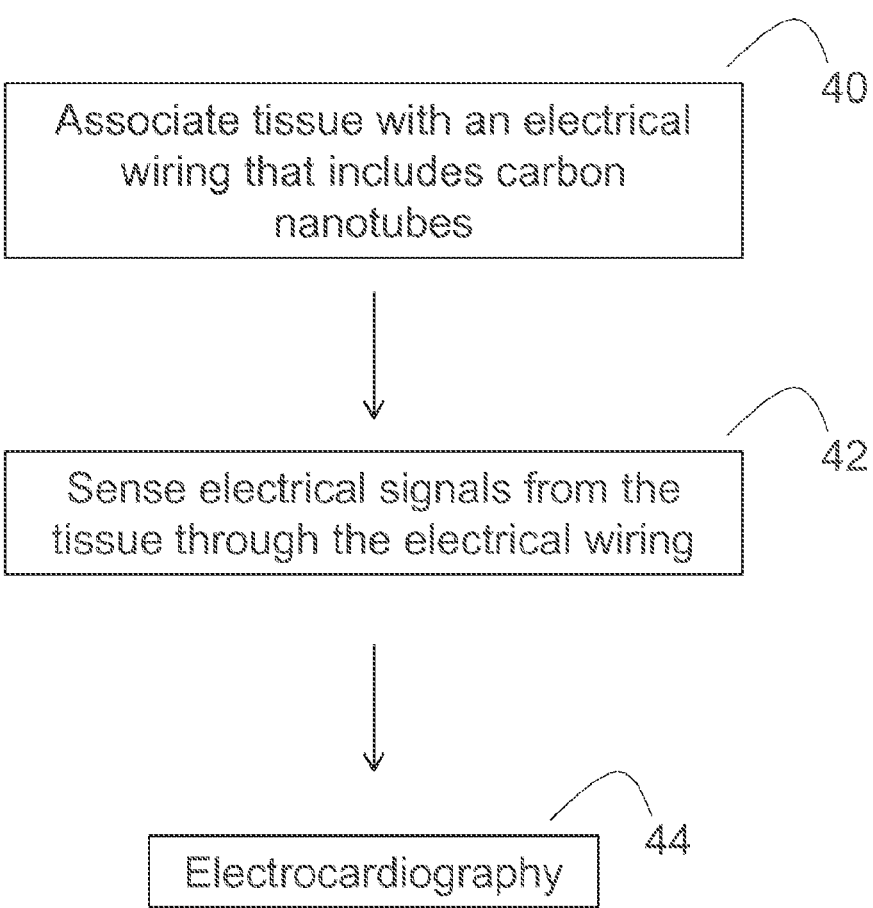

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, hut not limited to, patents, patent applications, articles, hooks, and treatises, are, hereby expressly incorporated herein by reference in their entirety for any purpose. In the event that one or more of the incorporated literature and similar materials defines a term in a manner that contradicts the definition of that term in this application, this application controls.

Disruption in normal electrical cardiac conduction leads to slowed conduction zones (SZC's). These SZC's provide the substrate for numerous forms of cardiac arrhythmia, mainly those utilizing re-entry as their primary mechanism. Existing treatment methods cannot restore normal conductive function to these SZC's. Several treatment methods for cardiac arrhythmia work by modifying the conduction speed of the rest of the myocardial tissue to counteract the effects of SZC's. For instance, anti-arrhythmic treatment methods include administration of drugs that modify the speed of conduction in myocardial tissue, Such treatment methods are also conducted by controlled and localized deactivation of some areas of the heart (i.e., catheter ablation). Anti-arrhythmic therapies have, also included ablation of impaired areas. However, ablation irreversibly causes permanent scarring of the heart without addressing the mechanism of reentrant arrhythmias, such as conduction slowing.

Furthermore, the aforementioned anti-arrhythmic therapies demonstrate varied and limited efficacies in different patient populations. Such anti-arrhythmic therapies may also involve further slowing or elimination of conduction, either by increasing the cardiac electrical refractory periods or cardiac ablation.

Current methods of sensing electrical signals from cardiac tissues and transmitting electrical signals to cardiac tissues also suffer from numerous limitations. For instance, current implantable electrodes for pacemakers are usually millimeter-size metal leads. Because these electrodes are bulky and invasive, the process of insertion and removal can cause extensive damage to nearby tissue. The current metal electrodes are also subject to degradation and bending fatigue.

Various embodiments of the present disclosure address the aforementioned limitations. In some embodiments, the present disclosure pertains to methods of improving electrical conduction across an impaired region of a tissue. In some embodiments, the present disclosure pertains to methods of treating or preventing cardiac arrhythmia in a subject. In some embodiments, the present disclosure pertains to methods of transmitting electrical signals to a tissue by associating the tissue with an electrical wiring that includes carbon nanotubes. In some embodiments, the present disclosure pertains to methods of sensing electrical signals from a tissue by associating the tissue with an electrical wiring that includes carbon nanotubes. In some embodiments, the present disclosure pertains to carbon nanotube-containing electrical wirings for sensing or transmitting electrical signals from a tissue. In some embodiments, the present disclosure pertains to suture threads that include carbon nanotubes.

Improvement of Electrical Conduction in Tissues

In some embodiments, the present disclosure pertains to methods of improving electrical conduction across an impaired region of a tissue. In some embodiments illustrated in FIG. 1A, such methods can include applying an electrically conductive material across the impaired region of the tissue (step 10). In some embodiments, the applying results in the association of the electrically conductive material with non-impaired regions of the tissue near the impaired region of the tissue (step 12). In some embodiments, the applying also results in the electrical connection of the non-impaired regions of the tissue near the impaired region of the tissue (step 14). Such methods result in the improvement of electrical conduction across the impaired region of the tissue (step 16).

An example of a system for improving electrical conduction across an impaired region of a tissue is shown in FIG. 1B. In this depiction, tissue 30 contains impaired region 32 between non-impaired regions 34 and 36. Electrically conductive material 38 is electrically connected to non-impaired regions 34 and 36 through sutures 40. This electrical connection improves electrical conduction across impaired region 32.

As set forth in more detail herein, methods of improving electrical conduction across an impaired region of a tissue may be applied to various tissues with various types of impaired regions. Moreover, various methods may be utilized to apply various types of electrically conductive materials to impaired regions of tissues. Furthermore, the electrical conduction of tissues across an impaired region of a tissue may be improved in various ways.

Tissues

The methods of the present disclosure may be utilized to improve electrical conduction in various tissues. In some embodiments, the tissue includes, without limitation, nerve tissue, muscle tissue, myocardial tissue, and combinations thereof. In some embodiments, the tissue includes a single tissue type. In some embodiments, the tissue includes multiple tissue types.

In some embodiments, the tissue includes myocardial tissue. In some embodiments, the myocardial tissue includes ventricular tissue. In some embodiments, the myocardial tissue includes an al tissue.

Impaired Regions of Tissues

The methods of the present disclosure may be utilized to improve electrical conduction across various impaired regions of tissues. In some embodiments, the impaired regions of tissues include at least one of a scarred area, an ablated area, a bruised area, a cut area, a lesion, and combinations thereof.

The impaired regions of tissues may have various shapes. For instance, in some embodiments, the impaired regions of tissues can be in the form of squares, circles, ovals, and combinations of such shapes.

The impaired regions of tissues may also be derived from various tissue types. For instance, in some embodiments, the impaired regions of tissues include a single tissue type. In some embodiments, the impaired regions of tissues include multiple tissue types. In some embodiments, the multiple tissue types can include nerve tissue and muscle tissue.

In some embodiments, the impaired regions of tissues include impaired myocardial tissue. In some embodiments, the impaired regions of tissues include impaired ventricular tissue, such as impaired left ventricular tissue. In some embodiments, the impaired regions of tissues include impaired atrial tissue, such as impaired right atrial tissue.

Impaired regions of tissues may exhibit various properties. For instance, in some embodiments, the impaired regions of tissues exhibit blocked or reduced electrical conduction. In some embodiments, the impaired regions of tissues exhibit blocked or reduced passage of a depolarization wave. In some embodiments, the impaired regions of tissues exhibit blocked or reduced transmission of ion voltages from cell to cell. In some embodiments, the impaired regions of tissues represent a slowed conduction zone (SZC). In some embodiments, the impaired regions of tissues exhibit blocked or impaired action potentials within cells. In some embodiments, the impaired regions of tissues are electrically inactive.

In some embodiments, the impaired regions of tissues exhibit blocked or reduced contraction. For instance, in some embodiments, the impaired regions of tissues contract at a delayed time relative to other regions of the tissue.

Application of Electrically Conductive Materials to Tissues

Various methods may be utilized to apply an electrically conductive material across an impaired region of a tissue. In some embodiments, the applying includes associating the electrically conductive material with non-impaired regions of the tissue near the impaired region of the tissue. In some embodiments, the non-impaired regions of the tissue are on opposite sides of an impaired region of the tissue (e.g., non-impaired regions 34 and 36 in FIG. 1B).

In some embodiments, non-impaired regions of tissues exhibit normal electrical conduction. For instance, in some embodiments, the non-impaired regions of tissues exhibit normal passage of a depolarization wave. In some embodiments, the non-impaired regions of tissues exhibit normal transmission of ion voltages from cell to cell. In some embodiments, the non-impaired regions of tissues exhibit normal action potentials within cells. In some embodiments, the non-impaired regions of tissues are electrically active. In some embodiments, the non-impaired regions of tissues exhibit normal contraction.

In some embodiments, the associating of electrically conductive materials with non-impaired regions of the tissue near an impaired region of the tissue results in the formation of a bridge across the impaired region of the tissue (e.g., electrically conductive material 38 in FIG. 1B). In some embodiments, the associating of electrically conductive materials with non-impaired regions of the tissue near an impaired region of the tissue results in the formation of an electrical connection across the impaired region of the tissue.

In some embodiments, the associating of electrically conductive materials with non-impaired regions of the tissue near an impaired region of the tissue occurs by implanting the electrically conductive materials into the non-impaired regions of the tissue. In some embodiments, the associating of electrically conductive materials with non-impaired regions of the tissue near an impaired region of the tissue occurs by suturing the electrically conductive materials into the non-impaired regions of the tissue (e.g., sutures 40 in FIG. 1B). In some embodiments, the suturing includes, without limitation, direct suturing, external suturing on the tissue, internal suturing within the tissue, and combinations thereof. In some embodiments, the electrically conductive materials may serve as the sutures.

In some embodiments, the associating of electrically conductive materials with non-impaired regions of the tissue near an impaired region of the tissue occurs by placing the electrically conductive material over a surface of the impaired region of the tissue. In some embodiments, the placement can include covering of the impaired region of the tissue, patching of the impaired region of the tissue, implanting the electrically conductive material over or through the impaired region of the tissue, and combinations thereof.

Electrically Conductive Materials

The methods of the present disclosure may utilize various types of electrically conductive materials. In some embodiments, suitable electrically conductive materials include materials with sufficiently low resistivity. In some embodiments, suitable electrically conductive materials include materials with sufficiently low contact impedance with a tissue. In some embodiments, suitable electrically conductive materials include materials that are able to effectively transfer electric current between regions of a tissue (e.g., transmission of myocardial action potentials between cells). In some embodiments, suitable electrically conductive materials include materials that allow natural conduction signals to be transmitted in such a way that re-entrant currents are avoided. In some embodiments, suitable electrically conductive materials include materials with sufficient flexibility to bend along with tissue contraction without damaging or putting significant pressure on nearby tissues. In some embodiments, suitable electrically conductive materials include materials with sufficient resistance to flex fatigue to undergo such bending for at least 10 million cycles without degradation or fracture.

In some embodiments, suitable electrically conductive materials include materials with a resistivity that ranges from about 100 μΩcm to about 1 μΩcm. In some embodiments, suitable electrically conductive materials include materials that have a contact impedance with a tissue that ranges from about 5 MOhm μm² to about 50 MOhm μm².

In some embodiments, suitable electrically conductive materials include, without limitation, fibers, wires, metal wires, foils, metal foils, conductive polymers, carbon nanotubes, materials made from carbon nanotubes, and combinations thereof. In some embodiments, the electrically conductive material is coated with an adhesive material. In some embodiments, the adhesive material includes, without limitation, polyethylene glycol (PEG), chitosan, sucrose solutions, gelatin, and combinations thereof. In some embodiments, the adhesive material is biodegradable. In some embodiments, the electrically conductive material is uncoated.

The electrically conductive materials of the present disclosure may have various sizes. For instance, in some embodiments, the electrically conductive materials of the present disclosure include diameters that range from about 5 μm to about 5 mm. In some embodiments, the electrically conductive materials of the present disclosure include diameters that range from about 500 μm to about 1 mm. In some embodiments, the electrically conductive materials of the present disclosure include diameters that range from about 5 μm to about 500 μm. In some embodiments, the electrically conductive materials of the present disclosure include diameters that range from about 8 μm to about 200 μm.

The electrically conductive materials of the present disclosure may also have various shapes. For instance, in some embodiments, the electrically conductive materials of the present disclosure are in the form of fibers, films, patches, filaments, sheets, mesh, sutures, networks thereof, and combinations thereof. In some embodiments, the electrically conductive materials of the present disclosure are in the form of a mesh of network of filaments woven together. In some embodiments, the electrically conductive materials of the present disclosure are in the form of a woven network of filaments. In some embodiments, the electrically conductive materials of the present disclosure are in the form of a shape memory filament. In some embodiments, the electrically conductive materials of the present disclosure are in the form of thin conductive films, such as thin conductive carbon nanotube films. In some embodiments, the electrically conductive materials of the present disclosure are in the form of sutures, such as closed loops of sutures. In some embodiments, the electrically conductive materials of the present disclosure are in the form of wires. In some embodiments, the electrically conductive materials of the present disclosure are in the form of interwoven wires.

In some embodiments, the electrically conductive materials of the present disclosure include fibers. In some embodiments, the fibers include bundles of fibers. In some embodiments, the fibers include interwoven fibers. In some embodiments, the fibers include individual fibers.

In some embodiments, the electrically conductive materials of the present disclosure include carbon nanotubes. In some embodiments, the carbon nanotubes include, without limitation, single-walled carbon nanotubes, ultra-short single-walled carbon nanotubes, multi-walled carbon nanotubes, and combinations thereof.

In some embodiments, the electrically conductive materials of the present disclosure include carbon nanotube fibers. In some embodiments, the electrically conductive materials of the present disclosure only include carbon nanotube fibers. In some embodiments, the electrically conductive materials of the present disclosure consist essentially of carbon nanotube fibers. In some embodiments, the carbon nanotube fibers of the present disclosure include the carbon nanotube fibers disclosed in U.S. Pat. No. 7,125,502. In some embodiments, the carbon nanotube fibers of the present disclosure include the carbon nanotube fibers disclosed in U.S. patent application Ser. No. 12/740,529.

The carbon nanotube fibers of the present disclosure may be fabricated by various methods. For instance, in some embodiments, carbon nanotube fibers of the present disclosure are fabricated by spinning high concentration carbon nanotube solutions out of an orifice and into a coagulant bath by a previously patented process. See, e.g., U.S. Pat. No. 7,125,502. Also see U.S. patent application Ser. No. 12/740, 529. The carbon nanotube fibers (single or in bundles) can then be used to fabricate electrically conductive materials with a desired morphology. Moreover, the carbon nanotube fibers can be post-processed and customized for a specific use (e.g., coating with insulating polymers). In some embodiments, the carbon nanotube fibers of the present disclosure can also be manufactured with other types of carbon nanotube fibers, such as carbon nanotube fibers spun by direct spinning.

In some embodiments, the carbon nanotube fibers of the present disclosure include, without limitation, individual carbon nanotubes fibers, interwoven carbon nanotube fibers, coated carbon nanotube fibers, uncoated carbon nanotube fibers, aligned carbon nanotube fibers, bundles of carbon nanotube fibers, and combinations thereof.

In some embodiments, the electrically conductive materials of the present disclosure include single-walled carbon nanotube fibers. In some embodiments, the electrically conductive materials of the present disclosure include fibers of aligned single-walled carbon nanotubes.

In some embodiments, the electrically conductive materials of the present disclosure include multi-walled carbon nanotube fibers. In some embodiments, the electrically conductive materials of the present disclosure include fibers of aligned multi-walled carbon nanotubes.

In some embodiments, the carbon nanotube fibers of the present disclosure include diameters that range from about 5 μm to about 5 mm. In some embodiments, the carbon nanotube fibers of the present disclosure include diameters that range from about 500 μm to about 1 mm. In some embodiments, the carbon nanotube fibers of the present disclosure include diameters that range from about 5 μm to about 500 μm. In some embodiments, the carbon nanotube fibers of the present disclosure include diameters that range from about 8 μm to about 200 μm.

Improvement of Electrical Conduction in Tissues

The methods of the present disclosure can improve electrical conduction across an impaired region of a tissue by various mechanisms. For instance, in some embodiments, an electrically conductive material can improve the electrical conduction across an impaired region of a tissue by electrically connecting non-impaired regions of the tissue near the impaired region of the tissue. In some embodiments, the electrically conductive materials of the present disclosure electrically connect one side of the impaired region of a tissue to another side of the impaired region of the tissue. In some embodiments, the electrical connection is longitudinal.

In some embodiments the electrical connection of non-impaired regions of the tissue near the impaired region of the tissue results in transmittal of electrical currents across an impaired region of a tissue. In some embodiments, the electrical connection results in transduction of action potentials across an impaired region of a tissue (e.g., transduction of myocardial action potentials across impaired myocardial tissues).

In some embodiments, the electrical connection results in the transmittal of ion-regulated voltage signals across an impaired region of a tissue. In some embodiments, the transmitted voltage signals may be associated with depolarization. In some embodiments, a wave of depolarization moving through a tissue would reach the electrically conductive material and result in a voltage drop across the conductive material (due to the difference in electric potential between "depolarized" tissue and "polarized" tissue in contact with opposite sides of the electrically conductive material). This voltage drop can subsequently initiate depolarization of the tissue both within the impaired region and non-impaired regions of the tissue, thereby allowing the depolarization wave to proceed through the impaired region of the tissue with little or no change in speed relative to its passage in other regions of the tissue. In some embodiments, the transmitted voltage signals may be associated with depolarization in a myocardial tissue in connection with a heartbeat.

In some embodiments, the electrically conductive material improves electrical conduction across an impaired region of a tissue by restoring electrical conduction across an impaired region of a tissue. In some embodiments, the restoration of electrical conduction includes normalization of electrical conduction across an impaired region of a tissue. In some embodiments, the restoration of electrical conduction includes restoration of normal electrical conduction pathways across an impaired region of a tissue. In some embodiments, the restoration of electrical conduction includes restoration of normal electrical conduction velocities. In some embodiments, the restoration of electrical conduction includes restoration of synchronized contraction of an impaired region of a tissue.

In some embodiments, the electrically conductive material improves the electrical conduction across an impaired region of a tissue by enhancing electrical conduction across the impaired region of the tissue. In some embodiments, electrical conduction is enhanced by about 10% to about 95%. In some embodiments, electrical conduction is enhanced by about 10% to about 50%. In some embodiments, electrical conduction is enhanced by about 10% to about 25%. In some embodiments, electrical conduction is enhanced by about 15% to about 20%.

In some embodiments, the electrically conductive material improves the electrical conduction across an impaired region of a tissue by decreasing electrical current conduction time across the impaired region of the tissue. In some embodiments, electrical conduction time is reduced by about 10% to about 50 In some embodiments, electrical conduction time is reduced by about 10% to about 25%. In some embodiments, electrical conduction time is reduced by about 15% to about 20%. In some embodiments, electrical conduction time is reduced by about 1 ms to about 20 ms. In some embodiments, electrical conduction time is reduced by about 2 ms to about 10 ms.

Treatment or Prevention of Cardiac Arrhythmia

In some embodiments, the present disclosure pertains to methods of treating or preventing cardiac arrhythmia in a subject. In some embodiments, the aforementioned methods of improving electrical conduction across an impaired region of a tissue may be utilized to treat or prevent cardiac arrhythmia in a subject. In some embodiments illustrated in FIG. 1C, such methods can include applying an electrically conductive material across an impaired region of a tissue in a subject (step 20). In some embodiments, the applying results in the association of the electrically conductive material with non-impaired regions of the tissue near the impaired region of the tissue in the subject (step 22). In some embodiments, the applying also results in the electrical connection of the non-impaired regions of the tissue near the impaired region of the tissue in the subject (step 24). In some embodiments, the applying also results in the improvement of electrical conduction across the impaired region of the tissue in the subject (step 26). Such methods result in the treatment or prevention of cardiac arrhythmia in a subject (step 28).

As set forth previously, the methods of the present disclosure may be applied to various tissues with various types of impaired regions. For instance, in some embodiments, the tissue includes myocardial tissue, such as ventricular tissue or atrial tissue. In some embodiments, the impaired regions of tissues include impaired myocardial tissue, such as impaired ventricular tissue (e.g., impaired left ventricular tissue) or impaired atrial tissue (e.g., impaired right atrial tissue).

As also set forth previously, various methods may be utilized to apply various types of electrically conductive materials across impaired regions of tissues. As also set forth previously, the applying can result in the association of electrically conductive materials with non-impaired regions of a tissue near the impaired region of the tissue in various manners. As also set forth previously, the applying can result in the electrical connection of non-impaired regions of a tissue near the impaired region of the tissue in the subject in various manners. Furthermore, the electrical conduction of tissues may be improved in various ways that were described previously. As set forth in more detail herein, the treatment or prevention methods of the present disclosure may be utilized to treat or prevent various types of cardiac arrhythmias in various subjects.

Subjects

The treatment or prevention methods of the present disclosure may be applied to various subjects. In some embodiments, the subject is at risk of suffering from cardiac arrhythmia. In some embodiments, the subject is suffering from cardiac arrhythmia.

In some embodiments, the subject may be a non-human animal, such as mice, rats, other rodents, or larger mammals, such as dogs, monkeys, pigs, sheep, cattle and horses. In some embodiments, the subject may be a mammal, such as a sheep.

In some embodiments, the subject is a human being. In some embodiments, the subject is a human being at risk of suffering from cardiac arrhythmia. In some embodiments, the subject is a human being suffering from cardiac arrhythmia.

Cardiac Arrhythmias

In some embodiments, the methods of the present disclosure are utilized to treat cardiac arrhythmia. In some embodiments, the methods of the present disclosure are utilized to prevent cardiac arrhythmia. In some embodiments, the methods of the present disclosure are utilized to treat and prevent cardiac arrhythmia.

The methods of the present disclosure may be utilized to treat or prevent various types of cardiac arrhythmias. For instance, in some embodiments, the cardiac arrhythmia is ventricular arrhythmia. In some embodiments, the cardiac arrhythmia is atrial arrhythmia.

The methods of the present disclosure can be utilized to treat or prevent cardiac arrhythmia by various mechanisms. For instance, in some embodiments, cardiac arrhythmia is treated or prevented by normalizing the heart rhythm of a subject. In some embodiments, cardiac arrhythmia is treated or prevented by improving the heart rhythm of a subject.

In some embodiments, the heart's rhythm is normalized by improving conduction in zones of slowed or diseased myocardial conduction. In some embodiments, this improved conduction may have an anti-arrhythmic effect by increasing the "wavelength" of the re-entrant arrhythmic circuit, thereby improving conduction velocity and increasing the "wavelength" (i.e., a product of conduction velocity and refractory period), It is envisioned that any maneuver that increases the wavelength renders a greater tissue requirement for sustaining arrhythmia, thus rendering its sustenance less likely.

Electrical Wirings

In some embodiments, the present disclosure pertains to an electrical wiring. In some embodiments, the electrical wiring can be utilized to sense electrical signals from a tissue or transmit electrical signals to a tissue. In some embodiments, the electrical wiring includes carbon nanotubes. In some embodiments, the electrical wirings of the present disclosure consist essentially of carbon nanotubes. In some embodiments, the electrical wirings of the present disclosure only contain carbon nanotubes.

Carbon Nanotubes

The electrical wirings of the present disclosure may include various types of carbon nanotubes. For instance, in some embodiments, the carbon nanotubes can include, without limitation, single-walled carbon nanotubes, ultra-short single-walled carbon nanotubes, multi-walled carbon nanotubes, and combinations thereof.

In some embodiments, the carbon nanotubes of the electrical wirings of the present disclosure are coated with an adhesive material. In some embodiments, the adhesive material includes, without limitation, polyethylene glycol (PEG), chitosan, sucrose solutions, gelatin, and combinations thereof. In some embodiments, the adhesive material is biodegradable. In some embodiments, the carbon nanotubes of the electrical wirings of the present disclosure are uncoated.

In some embodiments, the carbon nanotubes of the electrical wirings of the present disclosure are in the form of carbon nanotube fibers (as described previously). In some embodiments, the electrical wirings of the present disclosure consist essentially of carbon nanotube fibers. In some embodiments, the electrical wirings of the present disclosure only contain carbon nanotube fibers. In some embodiments, the carbon nanotube fibers include, without limitation, single-walled carbon nanotube fibers, multi-walled carbon nanotube fibers, aligned carbon nanotubes fibers, and combinations thereof.

In some embodiments, the carbon nanotube fibers of the electrical wirings of the present disclosure include diameters that range from about 5 μm to about 5 mm. In some embodiments, the carbon nanotube fibers include diameters that range from about 500 μm to about 1 mm. In some embodiments, the carbon nanotube fibers include diameters that range from about 5 μm to about 500 μm. In some embodiments, the carbon nanotube fibers include diameters that range from about 8 μm to about 200 μm.

Electrical Wiring Configurations

The electrical wirings of the present disclosure can have various shapes. For instance, in some embodiments, the electrical wirings of the present disclosure include a conductive element and a point of attachment. In some embodiments, the conductive element is in the form of a wire or fiber. In some embodiments, the point of attachment is in the form of an adhesive patch or an electrode. In some embodiments, the point of attachment is in the form of an electrode. In some embodiments, the electrical wiring includes a plurality of points of attachment.

In some embodiments, the conductive element includes carbon nanotubes, such as carbon nanotube fibers. In some embodiments, the point of attachment includes carbon nanotubes, such as carbon nanotube fibers. In some embodiments, the conductive element and the point of attachment both include carbon nanotubes, such as carbon nanotube fibers.

In some embodiments, the electrical wirings of the present disclosure may be associated with an electrical device. In some embodiments, the electrical device includes, without limitation, medical devices, pacemakers, defibrillators, electrocardiographs, and combinations thereof. In some embodiments, the electrical device is a pacemaker. In some embodiments, the electrical device is a defibrillator. In some embodiments, the electrical device is an implantable cardioverter defibrillator (ICD).

An example of an electrical wiring associated with an electrical device is illustrated in FIG. 1D, In this example, electrical wiring 10 includes conductive element 12 and point of attachment 14. Conductive element 12 in this example can be in the form of a fiber, such as a carbon nanotube fiber. Likewise, point of attachment 14 can be in the form of an electrode, such as an electrode containing carbon nanotubes. Conductive element 12 is associated with electrical device 20 while point of attachment 14 is associated with subject 16.

As set forth in more detail herein, the electrical wirings of the present disclosure may be utilized to transmit electrical signals to various tissues. As also set forth in more detail herein, the electrical wirings of the present disclosure may be utilized to sense various electrical signals from various tissues.

Methods of Transmitting Electrical Signals to a Tissue

In some embodiments, the present disclosure pertains to methods of transmitting electrical signals to a tissue. In some embodiments illustrated in FIG. 1E, the method involves associating the tissue with an electrical wiring that includes carbon nanotubes (step 30). In some embodiments, the method also involves transmitting electrical signals to the tissue through the electrical wiring (step 32). In some embodiments, such methods may be utilized for cardiac defibrillation (step 34) or cardiac resynchronization (step 36).

The transmittal methods of the present disclosure may utilize various types of electrical wirings. Suitable electrical wirings were disclosed previously. As set forth in more detail herein, various methods may be utilized to associate various types of electrical wirings with various types of tissues. Moreover, various types of electrical signals may be transmitted to tissues from various electrical devices.

Tissues

The electrical wirings of the present disclosure may be associated with various types of tissues. In some embodiments, the tissue includes, without limitation, nerve tissue, muscle tissue, myocardial tissue, and combinations thereof. In some embodiments, the tissue includes a single tissue type. In some embodiments, the tissue includes multiple tissue types. In some embodiments, the tissue includes myocardial tissue. In some embodiments, the myocardial tissue includes ventricular tissue or atrial tissue.

In some embodiments, the tissue is an isolated tissue. In some embodiments, the tissue is part of a subject. In some embodiments, the subject is at risk of suffering from cardiac arrhythmia. In some embodiments, the subject is suffering from cardiac arrhythmia.

In some embodiments, the subject may be a non-human animal, such as mice, rats, other rodents, or larger mammals, such as dogs, monkeys, pigs, sheep, cattle and horses. In some embodiments, the subject may be a mammal, such as a sheep.

In some embodiments, the subject is a human being. In some embodiments, the subject is a human being at risk of suffering from cardiac arrhythmia. In some embodiments, the subject is a human being suffering from cardiac arrhythmia.

Association of Tissues with Electrical Wirings

Various methods may be utilized to associate tissues with electrical wirings. For instance, in some embodiments, the associating includes implanting the electrical wiring into the tissue. In some embodiments, the associating includes suturing the electrical wiring into the tissue. In some embodiments, the associating includes adhering the electrical wiring to or nearby the tissue. In some embodiments, the associating forms an electrical interface between the electrical wiring and the tissue.

In some embodiments, the associating includes directly associating the electrical wiring with a tissue. In some embodiments, the associating includes indirectly associating the electrical wiring with a tissue. For instance, in some embodiments, the associating includes indirectly associating an electrical wiring with myocardial tissue by placing a point of attachment of the electrical wiring on the skin of a subject near the myocardial tissue (See, e.g., FIG. 1D).

Transmittal of Electrical Signals

Various methods may also be utilized to transmit electrical signals to a tissue. For instance, in some embodiments, the transmittal includes delivery of an electrical signal from an electrical device associated with an electrical wiring. In some embodiments, the electrical device includes, without limitation, medical devices, pacemakers, defibrillators, and combinations thereof.

Applications

The aforementioned methods of transmitting electrical signals to a tissue can be used for various purposes. For instance, in some embodiments where the tissue includes myocardial tissue in a subject, the methods of the present disclosure can be used for cardiac resynchronization in the subject. In some embodiments, the transmittal of electrical signals to the myocardial tissue includes delivery of a resynchronization shock from an electrical device (e.g., a pacemaker) associated with an electrical wiring. In some embodiments, the transmittal of electrical signals can be utilized for left ventricular pacing, control of heart beat rate at desired frequencies, and combinations thereof.

In some embodiments where the tissue includes myocardial tissue in a subject, the methods of the present disclosure can be used for defibrillation in the subject. For instance, in some embodiments, the methods of the present disclosure can be used for delivery of a defibrillation shock from an electrical device (e.g., a defibrillator) associated with an electrical wiring. In some embodiments, the transmittal of electrical signals can be used to treat cardiac dysrhythmias, ventricular fibrillation, pulseless ventricular tachycardia, and combinations thereof.

A Method of Sensing Electrical Signals from a Tissue

In some embodiments, the present disclosure pertains to methods of sensing electrical signals from a tissue. In some embodiments illustrated in FIG. 1F, the method involves associating the tissue with an electrical wiring that includes carbon nanotubes (step 40). In some embodiments, the method also involves sensing electrical signals from the tissue through the electrical wiring (step 42). In some embodiments, such methods may be utilized for electrocardiography (step 44).

The sensing methods of the present disclosure may utilize various types of electrical wirings. Suitable electrical wirings were disclosed previously. As also set forth previously, various methods may be utilized to associate various types of electrical wirings with various types of tissues in various subjects. Moreover, as set forth in more detail herein, various electrical signals may be sensed from tissues by various electrical devices.

For instance, in some embodiments, the sensing of electrical signals from a tissue includes sensing electrical signals in an electrical device associated with an electrical wiring. In some embodiments, the electrical device includes, without limitation, medical devices, pacemakers, defibrillators, electrocardiographs, and combinations thereof. In some embodiments where a tissue includes myocardial tissue in a subject, the sensing of electrical signals from the myocardial tissue in the subject includes sensing of cardiac electrical activity. In some embodiments, the sensing can be utilized for electrocardiography.

Suture Threads

In some embodiments, the present disclosure pertains to suture threads that include carbon nanotubes. In some embodiments, the suture threads of the present disclosure consist essentially of carbon nanotubes. In some embodiments, the suture threads of the present disclosure only contain carbon nanotubes.

The suture threads of the present disclosure may include various types of carbon nanotubes. For instance, in some embodiments, the carbon nanotubes can include, without limitation, single-wailed carbon nanotubes, ultra-short single-walled carbon nanotubes, multi-walled carbon nanotubes, and combinations thereof.

In some embodiments, the carbon nanotubes of the suture threads of the present disclosure are in the form of carbon nanotube fibers. In some embodiments, the carbon nanotube fibers include, without limitation, single-walled carbon nanotube fibers, multi-walled carbon nanotube fibers, aligned carbon nanotubes fibers, and combinations thereof. In some embodiments, the suture threads of the present disclosure consist essentially of carbon nanotube fibers. In some embodiments, the suture threads of the present disclosure only contain carbon nanotube fibers.

The suture threads of the present disclosure can have various diameters. For instance, in some embodiments, suture threads of the present disclosure include diameters that range from about 5 μm to about 5 mm. In some embodiments, the suture threads of the present disclosure include diameters that range from about 500 μm to about 1 mm. In some embodiments, the suture threads of the present disclosure include diameters that range from about 5 μm to about 500 μm. In some embodiments, the suture threads of the present disclosure include diameters that range from about 8 μm to about 200 μm.

The suture threads of the present disclosure can also have various lengths. For instance, in some embodiments, the suture threads of the present disclosure have lengths that range from about 1 m to about 1 mm. In some embodiments, the suture threads of the present disclosure have lengths that range from about 10 cm to about 100 mm. In some embodiments, the suture threads of the present disclosure have lengths that range from about 1 cm to about 1 mm.

Advantages

Various embodiments of the present disclosure provide numerous advantages and applications. For instance, because of their combination of electrical conductivity, mechanical strength, flexibility, fatigue resistance, and low contact impedance, the carbon nanotube fibers of the present disclosure can provide optimal materials for electrical wirings (e.g., functional electrodes). For instance, in some embodiments, the carbon nanotube fibers of the present disclosure can provide electrodes for pacing and sensing heart electric activity. In some embodiments, the carbon nanotube fibers of the present disclosure can also be used to restore cardiac conduction through electrically inactive cardiac scar. In the above applications, the carbon nanotube fibers of the present disclosure can be directly sutured on the myocardial tissue, either in external or intracardiac locations.

In some embodiments, the high electric conductivity carbon nanotube fibers of the present disclosure can be connected to any device for heart sensing/pacing, thereby enabling the bidirectional transmission of high quality electric signals. Moreover, due to their small, flexible, strong and electrically stable properties, the carbon nanotube fibers of the present disclosure can be sutured on the heart with a significant improvement of electrode/tissue contact, precision of sensing/pacing, and minimization of mechanical trauma to the tissue due to electrode insertion and motion.

Due to their flexibility and small size, the carbon nanotube fibers of the present disclosure can also follow the natural movement of a beating heart without causing scarring or other inflammatory responses. In some embodiments, the carbon nanotube fibers of the present disclosure can also be used to fabricate devices such as leads for implantable pacemakers, defibrillators, electrodes for electrocardiography (ECG), and conductive sutures for therapeutic purposes (e.g. treatment of arrhythmias).

To Applicants' knowledge, the present disclosure also provides a first example of an additive process for restoring cardiac conduction and the first example of a conductive suture. By enabling improved conduction, the carbon nanotube fibers of the present disclosure can allow a paradigm shift in treatment of cardiac arrhythmias. For the first time to Applicants' knowledge, Applicants can treat arrhythmias not by slowing or eliminating conduction (which often requires surgical destruction of cardiac tissue in a process called ablation or use of medications with multiple side effects and suboptimal efficacy), but by improving conduction.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1, Pacing and Sensing Myocardial Activation and Restoring Myocardial Conduction Velocity with CNT Fibers A series of experiments were performed on 4 sheep at the Texas Heart Institute in full concordance with IACUC guidelines. Three sheep were used to assess left ventricular (LV) conduction during LV pacing. Another sheep was used to assess right atrial (RA) conduction during non-paced, sinus rhythm. Myocardial conduction velocity was evaluated in all sheep.

The sheep were shaved, anesthetized, and intubated/ventilated. The vital signs of the sheep were monitored according to standard surgical procedures. A left lateral thoracotomy and a pericardial resection were performed to expose the epicardial surface of the heart. For the LV studies, the LV was exposed and lifted with stay stitches.

Figure 2:
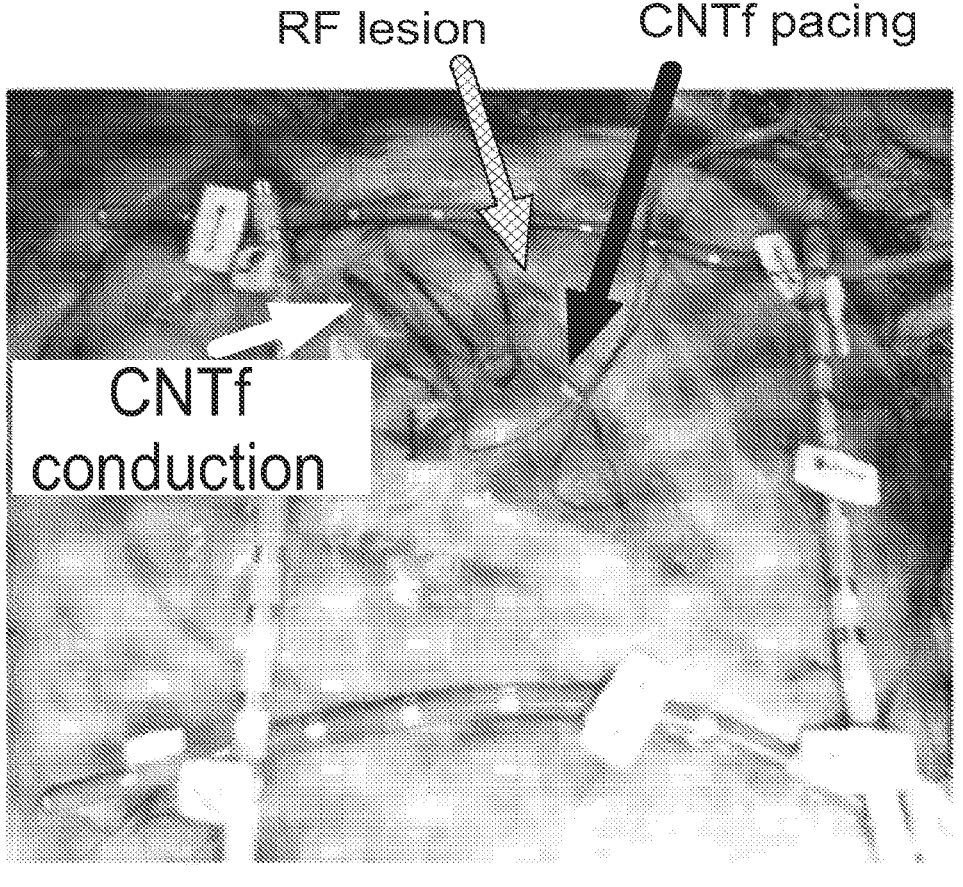
FIG. 2 shows experimental setups and data relating to the use of a carbon nanotube fiber (CNTf or CNT fibers) as an electrode configuration for restoring electrical conduction in cardiac tissues.
Figure 2:
Figure 2:
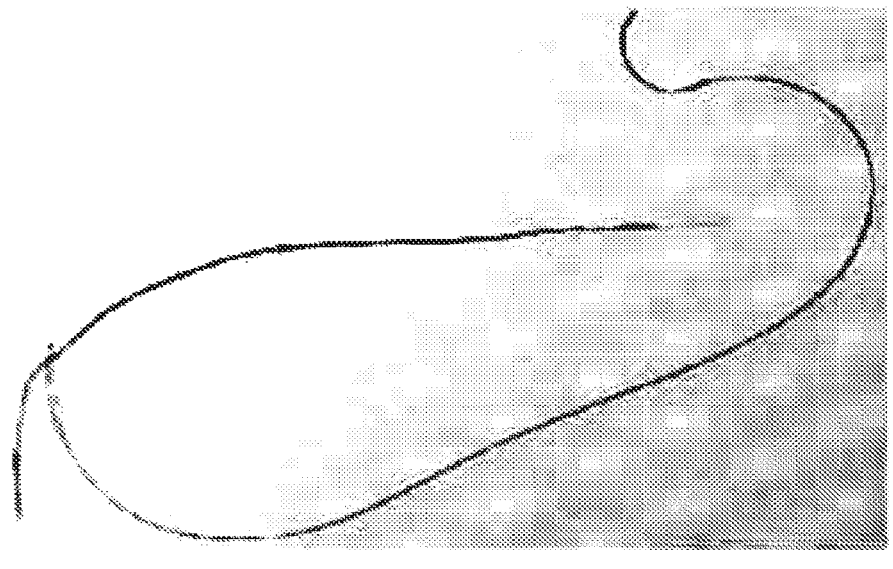
Figure 2:
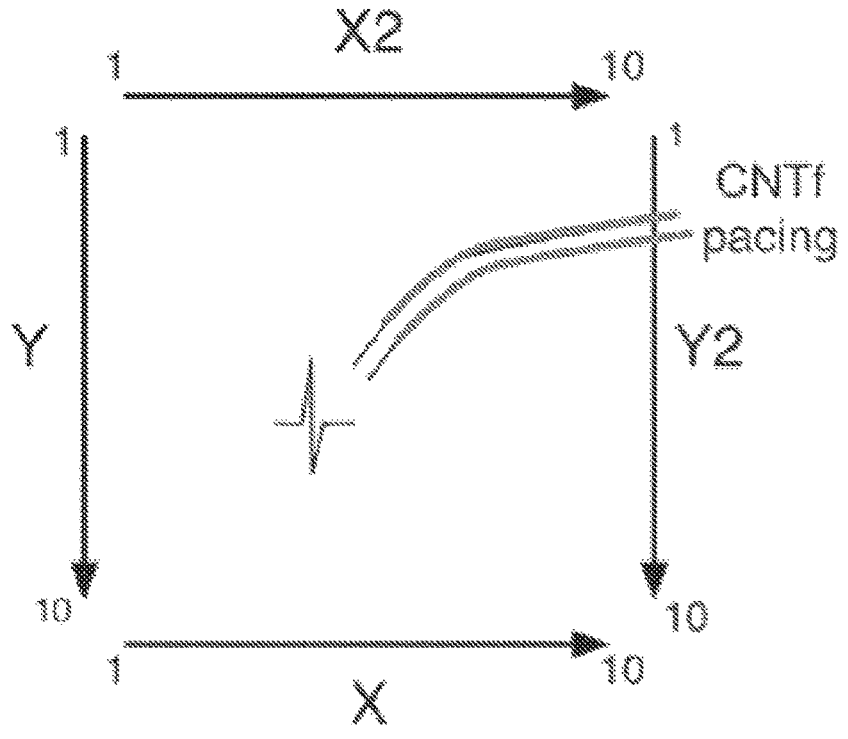
Figure 2:
Figure 2:
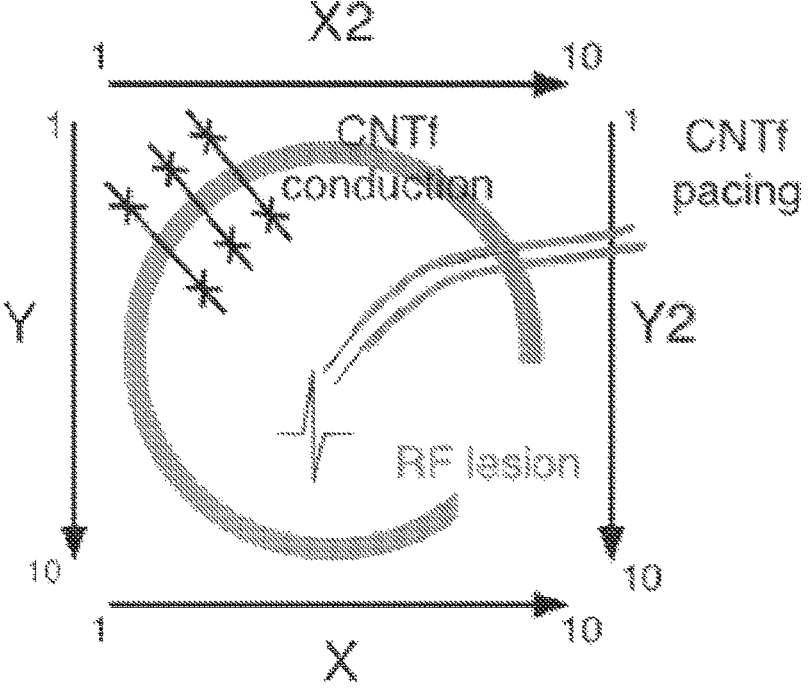

As shown in FIG. 2A, decapolar catheters were sutured to the LV epicardial surface in a square between the epicardial arteries overlying the LV (5×5 cm). Thereafter, insulated CNT fibers were sewn into the center of the square of myocardium assayed as pacing leads.

In two LV studies, insulated CNT fibers were also sewn onto the LV apex and used to detect myocardial activation. In all experiments, the polymer insulation was stripped from the CNT fibers at the point of contact with the tissue. Conduction times between the pacing wire and electrodes were measured at cycle length (CL) of 400 ms. For the RA study, a linear lesion parallel to the tricuspid valve was created and no pacing was performed so that it could be possible to assess whether CNT fibers can improve conduction during sinus (i.e., unpaced) heart rhythm.

To model anatomical conduction block, radiofrequency (RF) energy was used to create a C-shaped transmural scar that would allow one area of paced wavefront to exit from the scar (4:30 o'clock position), RE energy was applied with a Safire™ Blu™ or Thermocool irrigated ablation catheter (St. Jude Medical, St. Paul, MN and Biosense Webster, Diamond Bar, CA, respectively) at 30-40 watts for a total of 5 minutes. A scar-related increase in conduction time was confirmed by incremental ventricular pacing from baseline to cycle length of 400 ms.

In order to evaluate the effect of CNT fibers on conduction velocity, CNT fibers were sutured into the myocardium (FIG. 2A). The CNT fibers were sewn across the scar at the 10:30 o'clock position, 180 degrees from the scar opening. After placement, the pacing protocol was repeated, and conduction times from the CNT pacing wires to each electrode were measured. The CNT fibers were then removed, and a silk suture was tested as a negative control. The silk suture was used as a negative control because silk is a carbon-based organic fiber with physical and mechanical properties similar to those of CNT fibers without the conductivity of CNT fibers.

Figure 5:
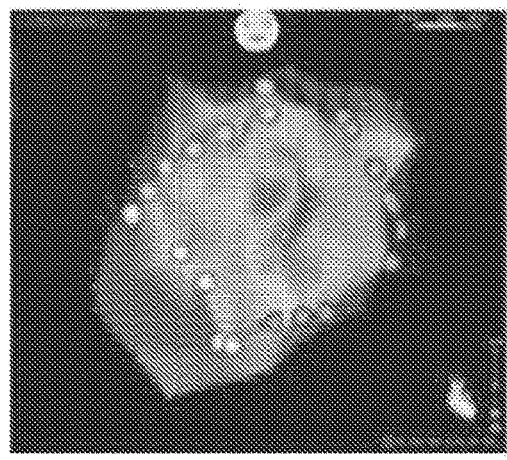
FIG. 5 shows local activation time maps of epicardial tissue. The image in FIG. 5B shows significant slowing of myocardial conduction across the C-shaped scar created by RF ablation (red dots pointed by red arrows) when compared to the baseline condition (FIG. 5A).
Figure 5:
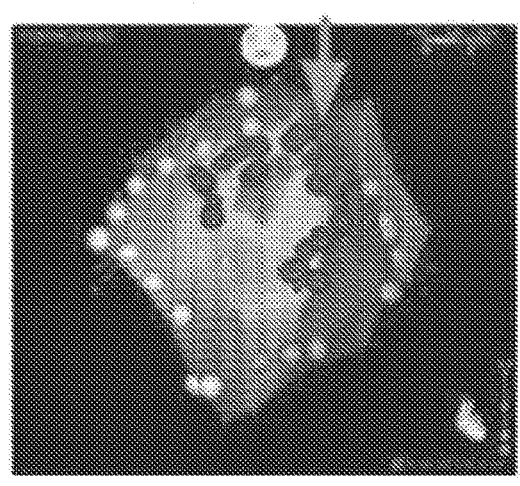
Figure 5:
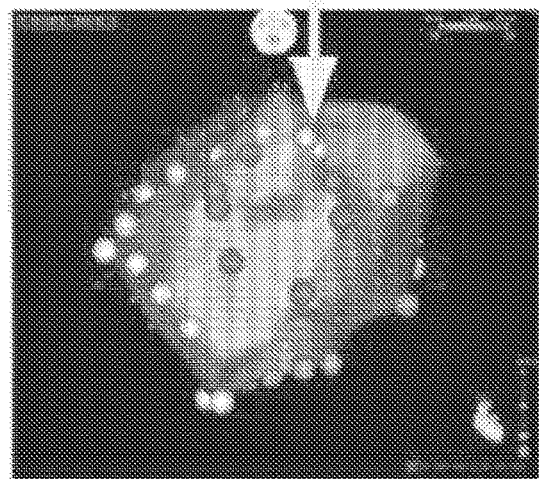

To determine whether sensed (non-paced currents) would also transfer across the wires, a fourth study was performed in which CNT fibers were placed in the RA. For this study, conduction delays and the changes associated with CNT fiber use were measured in sinus rhythm, in the absence of pacing. In addition to the epicardial electrode arrays, high-density epicardial activation mapping (60-80 points per condition) was performed in the last 2 studies (1 LV and 1 RA) by using the Carto 3 (Biosense Webster, Diamond Bar, CA) mapping system (FIG. 5). Mapping was conducted at baseline, after ablation, and after placement of the CNT fibers and silk control. Voltages and propagation/activation sequences were used to confirm alteration of the myocardial conduction velocity.

Example 1.1. Results

Figure 3:
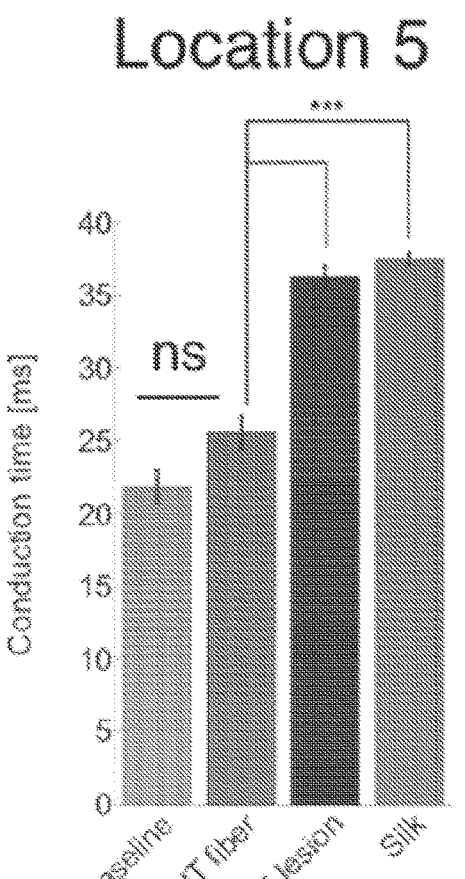
FIG. 3 shows that CNT fibers improve conduction time in areas of myocardial conduction block (i.e., areas of RE lesion). Histograms of conduction tunes at a pacing frequency of 150 beats per minute (BPM) CL 400 ms) in the locations proximal (11 o'clock) (FIG. 3A) and distal (2 o'clock) (FIG. 3B) to CNT fiber implants are shown. When the CNT fiber was implanted across the RE lesion, a significant improvement on conduction time compared to RE lesion and silk condition was measured at the 11 o'clock position (FIG. 3A), but not at the 2 o'clock position (FIG. 3B). A two way ANOVA test was used for effects of condition $F((1.1727, 27.634)=173.484, P<0.0005)$ and of locations $(F(1.1844, 29.500)=6.673, P<0.005)$. Post-hoc pairwise comparisons with Bonferroni correction was used to compare the different conditions. Values are presented as mean±S.E.M. ***p<0.001, ns=not significant.
Figure 3:
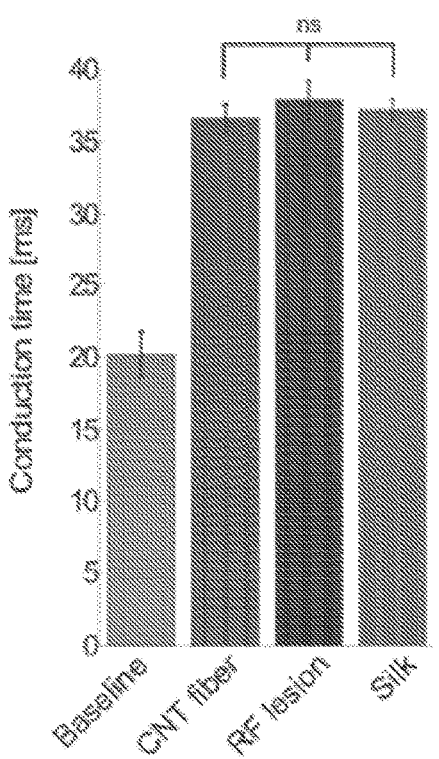
Figure 4:
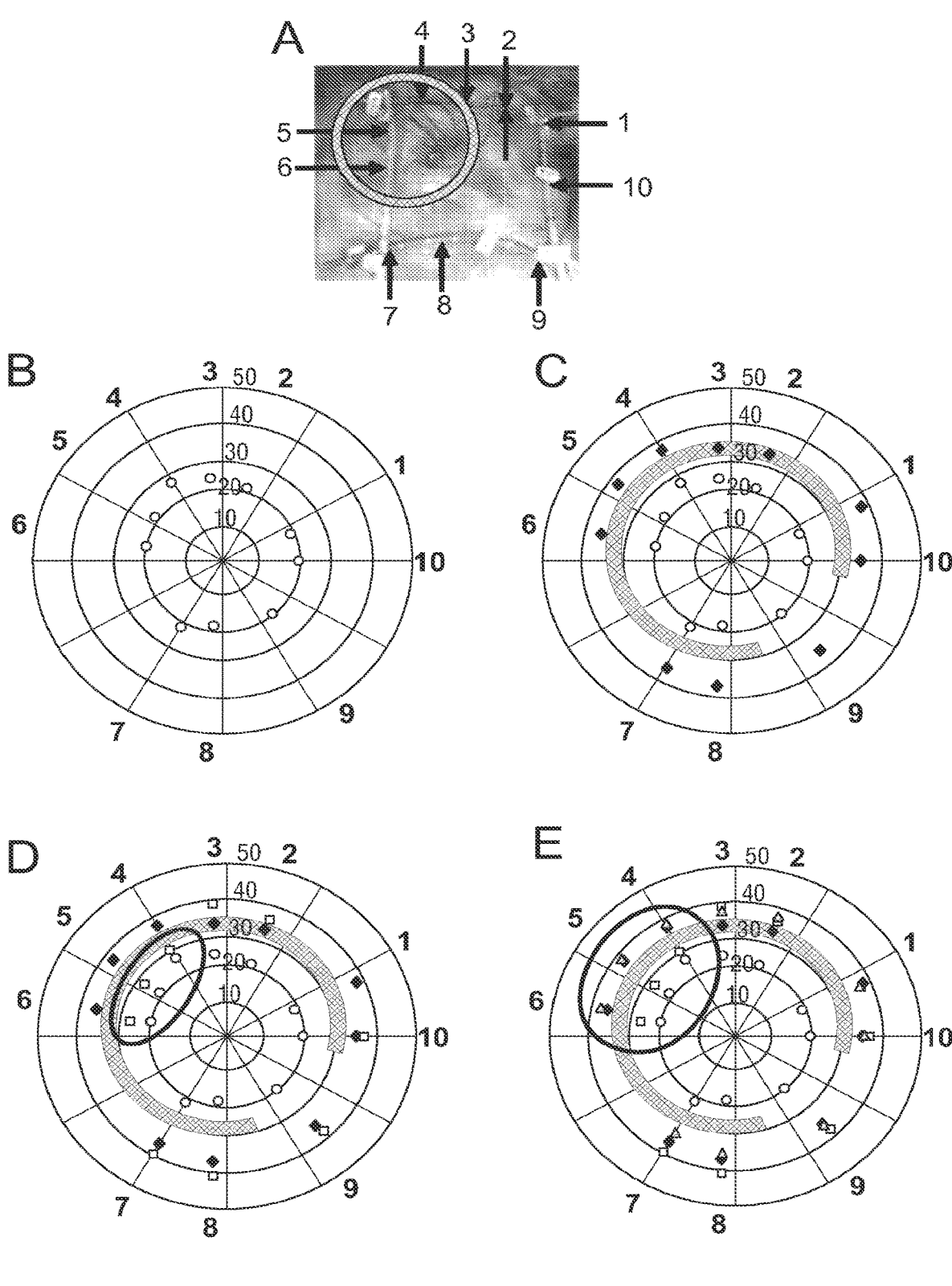
FIG. 4 shows conduction intervals measured across the entire RE ablated LV area shown in FIG. 2A.
Figure 7:
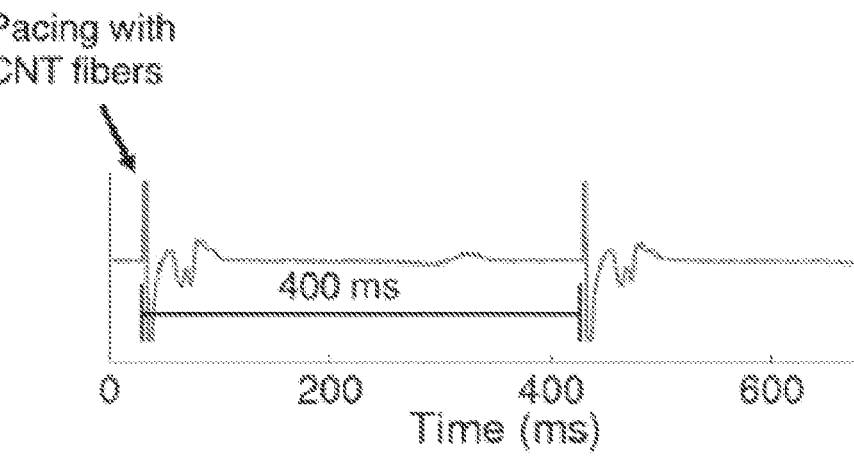
FIG. 7 shows data demonstrating myocardial pacing and sensing with CNT fibers.
Figure 7:
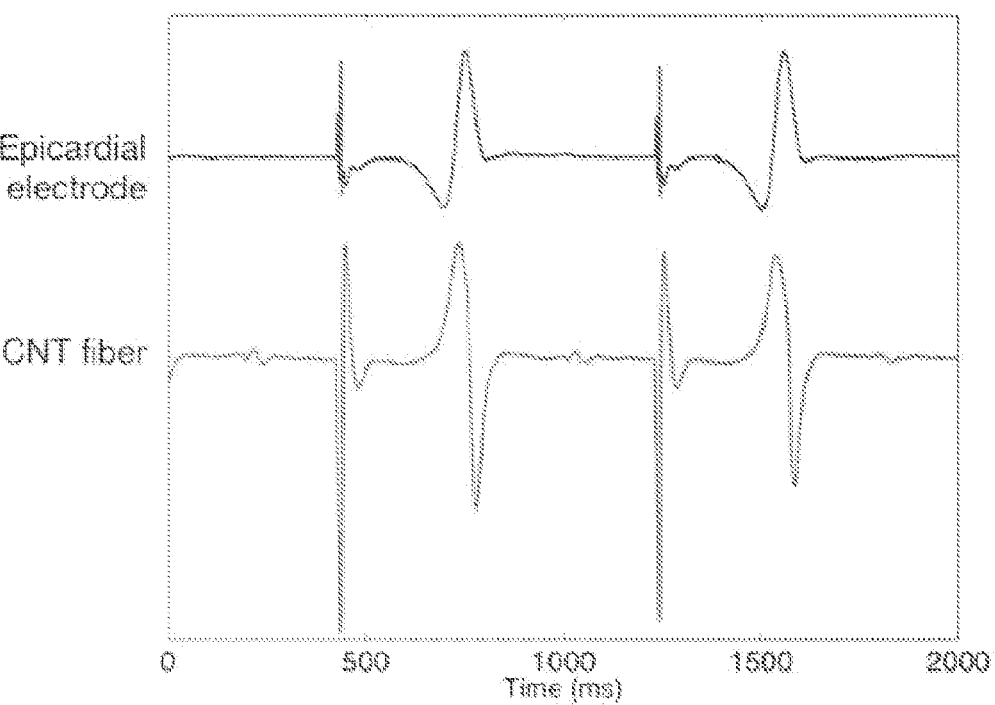

The average conduction time during CNT pacing of the LV myocardial tissue was 21.47±1.15 ms in the 11 o'clock position for the 3 animals tested. Creating a C-shaped transmural scar on the LV myocardium with RF ablation significantly increased conduction time across the scarred area in the 11 o'clock position (37.29±0.75 ms, FIG. 3A, p<0.001 versus baseline). Introducing CNT fibers across the LV scar in the 11 o'clock position significantly improved conduction time (26.35±0.89 ms, FIG. 3B, p<0.001 versus scar), Carto 3 imaging of the LV showed propagation of the wavefront through an isthmus overlaying the CNT fibers and bounded by the remaining scar tissue (FIG. 7). Placing a silk suture at the 11 o'clock position did not improve conduction time across the scarred myocardium (37.24±0.51 ms, FIG. 3A). This significant decrease in conduction time with CNT fibers compared to the RE scar condition was measured in the entire area proximal to the CNT fiber implant (FIG. 4), but not in the locations away from it. These results indicate that longitudinal conduction across a scar can be facilitated by CNT fibers but not by silk, an organic carbon-based fiber without the unique conductive properties of CNT fibers.

Figure 6:
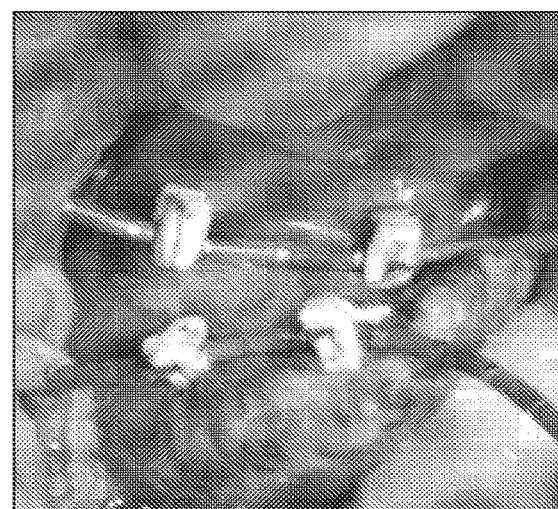
FIG. 6 shows improved sinus conduction with CNT fibers across an RF lesion in the right atrium.
Figure 6:
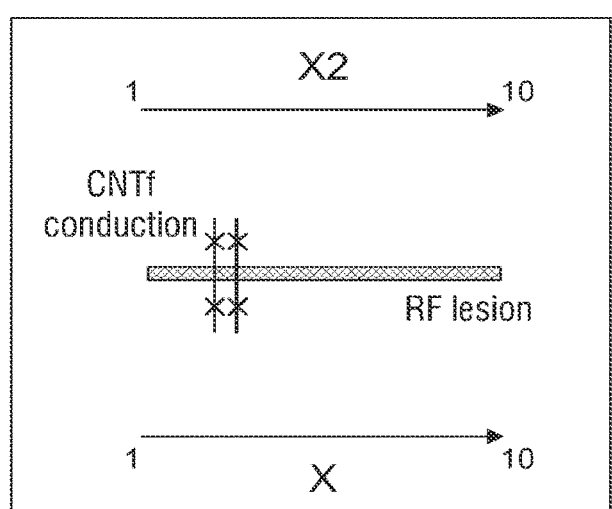
Figure 6:
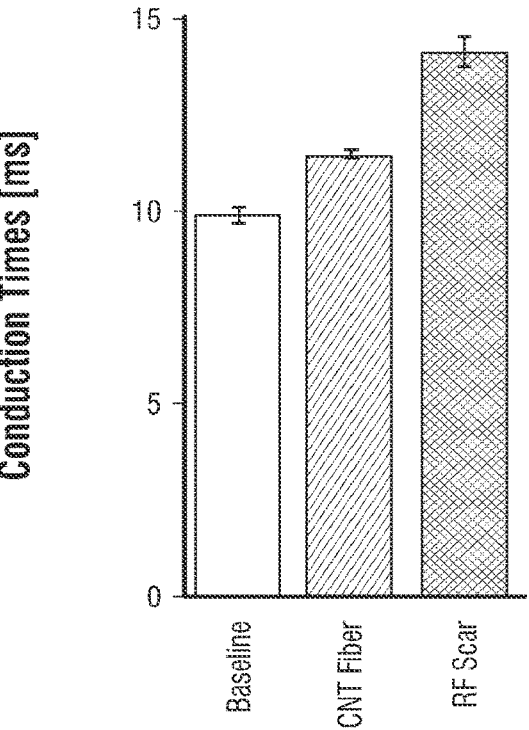

When the experiment was repeated in the RA using a linear scar between 2 decapolar catheters, sinus rhythm (and not pacing) was improved when CNT fibers were placed across the scar (FIG. 6). This preliminary study suggests that sinus rhythm alone may be sufficient to initiate conduction across CNT fibers.

In addition, when CNT fibers were used for LV pacing, the heart beat rate could be reliably controlled at the desired frequency throughout the entire experiment (FIG. 7A). Furthermore, optimal pacing thresholds (<0.2 m A) were obtained, even when pacing with a single CNT fiber filament.

When CNT fibers were used as sensing electrodes, myocardial activation could be reliably detected. Moreover, the average signal amplitude recorded after CNT fiber was introduced was two times higher than that recorded on the closest channel of the decapolar catheter (FIG. 7B).

These observations suggest a consistent and reliable electrical coupling between the CNT fibers and myocardial tissue. The observations also suggest that CNT fibers can be used to control and detect myocardial potentials.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of improving electrical conduction across an impaired region of a tissue, said method comprising:
   applying at least one electrically conductive wiring comprising two ends across the impaired region of the tissue,
   wherein the electrically conductive wiring has a diameter ranging from about 5 μm to about 500 μm,
   wherein the applying comprises associating the two ends of the electrically conductive wiring with non-impaired regions of the tissue near the impaired region of the tissue,
   wherein at least one of the non-impaired regions of the tissue generates an electrical signal,
   measuring, through the electrically conductive wiring, the electrical signal generated from the at least one of the non-impaired regions of the tissue,
   wherein the electrically conductive wiring transmits the electrical signal from one non-impaired region of the tissue to another non-impaired region of the tissue by bypassing the impaired region of the tissue, and
   wherein the electrical signal transmits an action potential from the one non-impaired region of the tissue to the another non-impaired region of the tissue.

2. The method of claim 1, wherein the tissue is selected from the group consisting of nerve tissue, muscle tissue, myocardial tissue, and combinations thereof.

3. The method of claim 1, wherein the tissue comprises myocardial tissue.

4. The method of claim 1, wherein the impaired region of the tissue comprises at least one of a scarred area, an ablated area, a bruised area, a cut area, a lesion, and combinations thereof.

5. The method of claim 1, wherein the impaired region of the tissue exhibits blocked or reduced electrical conduction.

6. The method of claim 1, wherein the impaired region of the tissue comprises impaired myocardial tissue.

7. The method of claim 1, wherein the associating occurs by suturing.

8. The method of claim 1, wherein the non-impaired regions of the tissue are on opposite sides of the impaired region of the tissue.

9. The method of claim 1, wherein the electrically conductive wiring is selected from the group consisting of fibers, wires, wires in the form of suturable threads, metal wires, foils, metal foils, conductive polymers, carbon nanotubes, materials made from carbon nanotubes, and combinations thereof.

10. The method of claim 1, wherein the electrically conductive wiring comprises fibers.

11. The method of claim 1, wherein the electrically conductive wiring comprises carbon nanotubes.

12. The method of claim 11, wherein the carbon nanotubes are selected from the group consisting of single-walled carbon nanotubes, ultra-short single-walled carbon nanotubes, multi-walled carbon nanotubes, and combinations thereof.

13. The method of claim 1, wherein the electrically conductive wiring comprises carbon nanotube fibers.

14. The method of claim 13, wherein the carbon nanotube fibers are selected from the group consisting of single-walled carbon nanotube fibers, multi-walled carbon nanotube fibers, aligned carbon nanotubes fibers, and combinations thereof.

15. The method of claim 1, wherein the electrically conductive wiring improves the electrical conduction across the impaired region of the tissue by electrically connecting non-impaired regions of the tissue near the impaired region of the tissue.

16. The method of claim 1, wherein the electrically conductive wiring improves the electrical conduction across the impaired region of the tissue by restoring or enhancing electrical conduction across the impaired region of the tissue.

17. The method of claim 1, wherein the electrically conductive wiring improves the electrical conduction across the impaired region of the tissue by decreasing electrical current conduction time across the impaired region of the tissue.

18. The method of claim 1, wherein the electrically conductive wiring has a low contact impedance with the tissue, wherein the low contact impedance ranges from about 5 MOhm $\mu m^2$ to about 50 MOhm $\mu m^2$.

19. The method of claim 1, wherein the electrically conductive wiring has a low resistivity that ranges from about 100 $\mu$Ohm cm to about 1 $\mu$Ohm cm.

20. The method of claim 1, wherein the electrically conductive wiring is associated with non-impaired regions of the tissue by suturing suture threads that include the electrically conductive wiring.

* * * * *